United States Patent [19]
Holbrook et al.

[11] Patent Number: 5,109,138
[45] Date of Patent: Apr. 28, 1992

[54] PROCESS AND CATALYST FOR HYDROHALOGENATION OF HYDROCARBONS

[75] Inventors: Michael T. Holbrook; Lawrence A. Hebert, both of Baton Rouge, La.; Stephen W. Najmy, Midland, Mich.; Ernest F. Stine, Jr., Knoxville, Tenn.; Reimer Hasche, Hammah, Fed. Rep. of Germany

[73] Assignee: The Dow Chemical Company, Midland, Mich.

[21] Appl. No.: 699,530

[22] Filed: May 14, 1991

Related U.S. Application Data

[63] Continuation-in-part of Ser. No. 529,009, May 24, 1990, abandoned.

[51] Int. Cl.⁵ .............................................. C07C 17/16
[52] U.S. Cl. .................................................... 570/258
[58] Field of Search ........................................ 570/258

[56] References Cited

U.S. PATENT DOCUMENTS

| | | | |
|---|---|---|---|
| 1,834,089 | 12/1931 | Carlisle | 570/258 |
| 4,464,880 | 8/1984 | Grunbein et al. | 570/258 |
| 4,935,565 | 6/1990 | Harley et al. | 570/258 |

OTHER PUBLICATIONS

Grinberg et al., "Characteristics of the Thermal Deactivation of Deposited Catalyst for Methyl Chloride Synthesis", Kinetikai Kataliz, vol. 28, No. 5, pp. 1273–1275, Sep.–Oct. 1987.

Glazunova et al., "Formation of Zinc Chloride Catalysts Based on $\gamma$—$Al_2O_3$", Kinetikai Kataliz, vol. 28, No. 5, pp. 1178–1182, Sep. –Oct. 1987.

Glazunova et al., "Study of Formation of $ZnCl_2$-NaCl-y-$Al_2O_3$ and $ZnCl_2$-KCl-$\gamma$-$Al_2O_3$ Catalytic Systems", Kinetikai Kataliz, vol. 28, No. 5, pp. 1183–1187, Sep.–Oct., 1987.

*Primary Examiner*—Howard T. Mars
*Assistant Examiner*—Kimberly J. Kestler

[57] ABSTRACT

A process for hydrohalogenating methanol with a hydrogen halide using a catalyst having an initial zone of lower activity and subsequent zones of higher activity so that coke formation and pressure drop are decreased and catalyst life is increased while overall high catalyst activity is maintained. One example of such a process uses a low surface area amorphous alumina in an initial zone and then progressively higher surface area alumina in subsequent zones.

8 Claims, No Drawings

PROCESS AND CATALYST FOR HYDROHALOGENATION OF HYDROCARBONS

CROSS REFERENCE TO RELATED APPLICATION

This is a continuation-in-part of co-pending application serial number 529,009, filed May 24, 1990 now abandoned.

BACKGROUND OF THE INVENTION

This invention relates to catalytic hydrohalogenation processes. In particular, the invention relates to the catalytic hydrohalogenation of hydrocarbyl compounds, such as methanol, to produce hydrocarbyl halides, such as methyl chloride.

Chlorinated hydrocarbons have various utilities as industrial chemicals and solvents. For example, methyl chloride is useful as a catalyst carrier in low temperature polymerizations; as a fluid for thermometric and thermostatic equipment; as a methylating agent in organic synthesis, such as the synthesis of methylcellulose; in the preparation of silicone rubbers; and as an extractant and low temperature solvent.

Methods for the production of halogenated, especially chlorinated, hydrocarbons, such as methyl chloride, are well-known. In a typical method for the production of methyl chloride, vaporized methanol and hydrogen chloride are mixed in approximately equimolar proportions and passed through a converter packed with a catalyst such as alumina gel or zinc chloride on activated carbon to form methyl chloride. Other known involve reactions in the liquid phase using an aqueous solution of catalyst. For example, U.S. Pat. No. 4,073,816 teaches that monochloroalkanes or monochlorocycloalkanes can be prepared by reacting an alcohol with hydrogen chloride in the presence of aqueous zinc chloride. German Offentlegungschrift 3332253 teaches that mixtures containing alcohols and ethers may be converted to alkyl halides by reactions with hydrogen chloride in the gas phase in the presence of an zinc chloride on aluminum oxide catalyst. This reference further teaches that small amounts of alkali metal chlorides and larger amounts of cadmium, iron and/or magnesium chlorides may be added with the zinc chloride to increase the efficiency of the catalyst.

Such methods do not resolve all the existing problems relating to the manufacture of chlorinated hydrocarbons. The problems include excessive production of byproducts; requirements for use of excess hydrochloric acid and excessive coking of the catalyst. An additional problem related to the use of alumina or alumina supported catalysts is the chemical breakdown of the alumina to produce other less desirable types of alumina such as boehmite, a monohydrate of alphaalumina, and also physical attrition. What is needed is a catalyst which results in a high yield of chlorinated hydrocarbyl compound which also permits the complete conversion of hydrochloric acid; which does not experience excessive coke formation; which reduces the amount of by-products formed; which decreases the formation of boehmite; and which is more resistant to attrition.

SUMMARY OF THE INVENTION

This invention comprises a vapor process for hydrohalogenating methanol with a hydrogen halide wherein a hydrohalogenation catalyst having at least two zones is used, wherein the first zone contains catalyst having lower activity and subsequent zones contain catalyst having progressively higher activity.

The process and catalyst provided by the present invention have been shown to decrease coke formation by lowering the peak reaction temperature, or reaction hot spot, while still providing high overall conversion to product. The decrease in the reaction hot spot in conjunction with successively more active catalyst zones have several benefits among which are increased production, decreased by-product formation and increased catalyst life.

DETAILED DESCRIPTION OF THE INVENTION

The process of vapor phase hydrohalogenation is often terminated because of high pressure drop in the reactor or low catalytic activity. High pressure drop results from coke formation on and around the catalyst which decreases space for gas flow. When an alumina catalyst is used, fracturing and powdering of the alumina catalyst also causes plugging. Loss of catalytic activity results from sintering and coke formation in general and additionally from boehmite formation when alumina catalysts are used.

The majority of coke formation in hydrohalogenation reactors is typically located in the initial zone of the catalyst bed where the temperature peaks. This is also known as the reactor hot spot. The hot spot has also been found to be the site where most catalyst sintering occurs and where the catalyst loses activity first and to the greatest degree.

The use of a catalyst having a lower activity in an initial contact zone reduces the hot spot in the hydrohalogenation reactor catalyst bed and thus reduces the formation of coke and increases catalyst life. It has surprisingly been found that the use of the low activity zone in combination with one or more subsequent zones having progressively increasing activity maintains or improves overall conversion and yield while still obtaining the benefits of lowering the reaction hot spot.

Control of catalyst activity is accomplished by (1) controlling catalyst surface area when using alumina itself as a catalyst and/or (2) controlling the catalyst concentration in a supported catalyst system.

One aspect of this invention is exemplified by the use of an amorphous alumina catalyst to hydrohalogenate methanol with hydrogen chloride. In this process the catalyst bed has multiple zones wherein the first zone has alumina having a surface area of from about 20 to about 100 $m^2/g$ and subsequent zones have increasingly larger surface areas. The total number of zones in the catalyst bed is at least two. The upper limit on the number of zones is primarily determined by the ability to mechanically construct the bed. Based on practical considerations, it is preferred that the catalyst bed have no more than ten zones, more preferably no more than six zones. It is most preferred that the catalyst bed have from two to four zones.

Practically speaking, most alumina hydrohalogenation catalysts have relatively high surface area. Such catalysts typically have a surface area greater than about 320 $m^2/g$ and such amorphous alumina catalysts are highly active.

In accord with a preferred embodiment of the present invention however, the reactor hot spot temperature is lowered and the reaction spread over a greater portion of the catalytic bed by using an amorphous alumina in a first zone comprising 10 to about 50 percent, more preferably from about 10 to about 30 percent, and most preferably from about 15 to about 25 percent of the catalytic bed. This initial contact catalyst zone comprises amorphous alumina having a surface area of 100 m$^2$/g or less, preferably from about 40 to about 100 m$^2$/g and more preferably from about 40 to about 70 m$^2$/g. A secondary zone of the catalytic bed in the hydrohalogenation reactor comprises from about 10 to about 50 percent, preferably from about 10 to about 30 percent, most preferably from about 15 to about 25 percent of the catalyst. This medium zone has amorphous alumina which has a surface area of from about 50 to about 150 m$^2$/g, more preferably from about 70 to about 150 m$^2$/g, and most preferably from about 80 to 130 m2/g. The remaining zone of the catalytic bed in the hydrohalogenation reactor comprises from about 0 to about 80 percent, more preferably from about 40 to about 80 percent and most preferably from about 50 to about 70 percent of the reactor. This zone of the catalyst comprises amorphous alumina having a surface area from about 150 to about 320 m$^2$/g, more preferably from about 150 to about 250 m2/g and most preferably from about 150 to about 220 m2/g. It should be noted that, while the ranges of catalyst surface areas given for the various catalyst zones overlap, selection of the surface area used in each case will be selected to result in each zone having different, progressively higher catalyst surface areas. It should also be noted that while a preferred embodiment showing three zones is set forth, other catalyst systems may comprise two, four or more beds having similar arrangements.

While such amorphous alumina materials may not be novel per se, and while some small portions of such amorphous aluminas may be found in other hydrohalogenation processes or literature references, it has not heretofore been known to combine relatively low surface area alumina in an initial contact zone with additional zones having progressively higher surface areas and wherein the high surface area has a limited range surface area to produce a catalytic bed which evidences a lower reactor hot spot temperature, increased catalyst life and decreased alumina phase transformation, decreased particle attrition and decreased coke forming tendencies while maintaining high overall conversion and yield. These advantages result in increased productivity, lower production costs and longer catalyst life.

A reduction in the surface area of amorphous alumina is an easily obtained result and is not a part of this invention. Further, preparation of a low surface area alumina is documented in the literature. In order to prepare alumina from crude aluminum hydroxide, one treatment is to calcine the material at 600°-800° C. until the surface area desired is obtained. High surface area aluminas, having greater than about 200 m2/g, can be readily obtained commercially. It is then only necessary to heat the alumina for a time sufficient to reduce the surface area, cool it and determine the resultant lowered surface area by conventional procedures. If the desired surface area has not been reached, the heating step is repeated until the desired surface area is obtained.

Any amorphous alumina can be employed in the present invention. However, beta, gamma, eta, chi and similar amorphbus aluminas are typically employed. The hydrated form of alumina, namely boehmite, produced by the action of water at lower temperatures in the hydrohalogenation process, is to be avoided because it is less efficient. Preferably, gamma alumina is employed as the catalyst in the present invention.

The alumina catalyst is not limited to any particular shape or size. Known and useful shapes include granules, flakes, spheres, tables, powder and extruded shapes such as rings, cylinders and lobes. Also the size of the catalyst employed is typically from about ⅛ inch (0.32 cm) to about ½ inch (1.27 cm). The shape and size of conventional catalysts used in hydrohalogenation reactions are useful in the present invention, being careful to follow general good engineering principles. For example, in a packed bed, the pressure drop across a bed of rings or lobed shapes is less than that of a sphere or extrudate shape of similar dimensions.

In a second embodiment of the present invention, it has been found that when the hydrohalogenation catalyst used is a supported catalyst, the use of different catalyst concentration levels and, optionally different supports, results in control of the catalyst activity. Catalyst activity is controlled by using different catalyst concentrations in the various zones of the catalyst with lowest concentration in the first zone and progressively greater concentration in the subsequent zone or zones. As is obvious, the subsequent zone or zones of the catalyst is that portion of the catalyst where secondary or subsequent contact occurs.

The supported catalyst useful in this embodiment of the present invention is advantageously a salt of a Group IA metal (alkali metal); a Group IIA or IIB, preferably Group IIB, metal: and a neutralizing number of counter anions supported on a non-alumina porous carrier material. Preferred Group IA metals include sodium, potassium, rubidium, lithium and cesium, with potassium and cesium being more preferred and potassium being most preferred. The preferred Group IIB metals include zinc, cadmium and mercury with zinc being more preferred. While any counter anion, such as bromide, chloride and fluoride, is suitable in the catalyst of this invention, the halides are preferred with chloride being most preferred. Other suitable anions are nitrates, sulfate, phosphate, acetates, oxylate and cyanides. Thus, a most preferred supported catalyst is a zinc chloride/potassium chloride catalyst.

The molar ratio of Group IA metal to Group IIA or IIB metal in the salt is preferably at least about 0.5:1 and no greater than about 1.5:1. It is more preferred that the molar ratio is at least about 0.9:1 and no greater than about 1.1:1 and most preferred that approximately equimolar portions of the two metals are used The amount of counter anion used is that which is sufficient to neutralize the cations of the salt.

Any support which will withstand the hydrochlorination conditions described herein can be used in the process of the present invention. Examples of appropriate supports include the well-known carbon supports such as activated carbon, carbon black, chars and coke. Alumina supports are also appropriate. Any amorphous alumina can be employed in the present invention. However, beta, gamma, eta, chi and similar amorphous aluminas are typically employed. The hydrated form of alumina, namely boehmite, produced by the action of water at lower temperatures in the hydrohalogenation process, is to be avoided because it is less efficient. Preferably, gamma alumina is employed as the catalyst support in the present invention. In particular, alumina supports having a surface area from about 25 m$^2$/g to about 320 m$^2$/g are preferred, with surface areas from about 40 to about 200 m2/g being more preferred. It is also preferred that alumina supports are designed such that the percent surface area and pore volume in the pore diameters below 50 angstroms, more preferably 100 angstroms, is minimized. Other suitable supports that may be used to support the catalyst include pumice, silica gel, asbestos, diatomaceous earth, fullers earth, titania, zirconia, magnesia, magnesium silicate, silicon carbide, silicalite, and silica. Of this latter group, a preferred support is silica. A silica having a surface area between 100 m2/g and 300 m2/g and a pore volume in the range of 0.75 cc/g to 1.4 cc/g is particularly suitable.

In a preferred embodiment, the supported catalyst used is a zinc chloride/potassium chloride catalyst. Practically speaking, zinc chloride/potassium chloride catalysts have significant activity for the conversion of alcohols such as methanol to organic halides such as methyl chloride. In accord with the present invention however, the reactor hot spot temperature is lowered and the reaction spread over a greater portion of the catalytic bed by the practice of this invention. This is accomplished by using a supported $ZnCl_2$/KCl catalyst having a specified lower concentration over the first about 10 to about 50 percent of the catalytic bed in an initial contact zone of the hydrohalogenation reactor. The subsequent zone or zones of the catalyst comprise from about 90 to about 50 percent of the catalytic bed wherein subsequent contact occurs. As discussed above in connection with the amorphous aluminum catalyst, the subsequent zone may be a single zone or may itself be divided into two or more zones. This subsequent zone or zones of the catalyst utilizes a supported $ZnCl_2$/KCl catalyst which has progressively higher catalyst concentration than the first zone of the catalyst. The use of such a catalyst system, having at least two zones results in a lower reactor hot spot temperature, increased catalyst life and decreased coke forming tendencies. These advantages result in increased productivity, lower production costs and longer catalyst life.

It is preferred that the concentration of the catalyst in the first zone of the catalyst bed is at least about one percent and no greater than about ten percent. The concentration in the second zone is preferably at least about five percent and no greater than about fifty percent. When more than two catalyst zones are used, the catalyst concentration in each subsequent zone increases over the preceding zone.

The catalyst system useful in the practice of this invention is not limited to any particular shape or size. Known and useful shapes include granules, flakes, spheres, tables, powder and extruded shapes such as rings, cylinders and lobes. Also the size of the catalyst employed is typically from about ⅛ inch (0.32 cm) to about ½ inch (1.27 cm). The shape and size of conventional catalysts used in hydrohalogenation reactions are useful in the present invention, being careful to follow general good engineering principles. For example, in a packed bed, the pressure drop across a bed of rings or lobed shapes is less than that of a sphere or extrudate shape of similar dimensions.

The salts are suitably supported on the carrier material by any standard impregnation technique such as that disclosed in Experimental Methods in Catalytic Research, Vol. II, edited by R. B. Anderson and P. T. Dawson, Academic Press, New York, 1978. A solution of both the Group IA and Group IIA or IIB metal cations and the associated anions may be employed to impregnate the support material or the metal salts may be impregnated from separate solutions. The resulting catalyst comprising the catalytically active salt and the support preferably comprises from about 1 to about 50 weight percent of the Group IIA or IIB metal salt, e.g., $ZnCl_2$, and from about 0.5 to about 30 weight percent of the Group IA metal salt, e.g., KCl, based on the percentage by weight of the total salts to the support. It is preferred to use at least about 20 and no greater than about 30 weight percent of the Group IIA or IIB metal salt and at least about 10 and no greater than about 20 weight percent of the Group IA metal salt and more preferred to use about 20 weight percent of the Group IIA or IIB metal salt and about 10 weight percent of the Group IIA metal salt. Preferred weight percents of the two salts are selected so as to result in approximately equimolar proportions of the Group IA and Group IIA or IIB salt being used.

The initial low activity zone of the catalyst and subsequent zones of increasing activity may be obtained by any combination of the catalyst zones described above. For example, a catalyst system of the present invention may comprise an initial zone of low surface area alumina, medium zone or zones of increasingly higher surface area alumina and a final very high activity zone of a supported catalyst on alumina. A particular benefit of the present invention is that zones of very high activity may be used in conjunction with the lower activity initial zone to result in a catalyst with very high overall activity in combination with long life.

The process of the present invention comprises contacting a lower alkanol such as methanol, ethanol or propanol and hydrogen chloride in the presence of the aforementioned catalyst systems under reaction conditions sufficient to produce the corresponding chlorinated hydrocarbon. It is preferred that the alkanol is methanol.

Molar ratios of lower alkanol to hydrogen halide, preferably hydrogen chloride, useful in the practice of this invention are generally at least about 1:10 and no greater than about 10:1. It is preferred that the molar ratio is from 1:5 to 5:1, more preferably 1:1.5 to 1.5:1. It is most preferred that the molar ratio approach stoichiometric, that is from 1:1.25 to 1.25:1.

The temperature range useful in the practice of this invention is any at which the hydrochlorination reaction will proceed. Preferably, the reaction is conducted at a temperature of at least about 25° C. and no greater than about 475° C. with at least about 175° C. to no greater than about 300° C. being more preferred. The most preferred temperature ranges from at least about 220° C. to no greater than about 280° C. Pressures typically employed in the process of the present invention are at least about atmospheric and no greater than about 500 psig. Preferred pressures are at least about 35 psig and no greater than about 150 psig.

Gas hourly space velocities (number of reactor volumes processed in stated time period) are suitably at least about 100 and no greater than about 10,000 hours$^{-1}$, preferably at least about 300 and no greater than about 3000 hr$^{-1}$.

The process may be operated in a batch mode or continuously although continuous operation is preferred. In a preferred embodiment, vaporized methanol and hydrogen chloride are added in approximately equimolar proportions to a fixed bed reactor containing the zoned catalyst of the present invention. The resultant products are separated by conventional means.

The present invention may comprise, consist essentially of or consist of the process described above and may be practiced in the absence of any step or element not specifically described.

The following examples are provided to illustrate the invention and should not be interpreted as limiting the invention in any manner. Unless otherwise indicated, all parts and percentages are by weight. The experimental data obtained are in connection with a hydrochlorination reaction carried out in a 20 foot (6.1 meter) vertical 1¼ inch (3.18 cm) diameter Inconel tube into which is placed the alumina catalyst as described in each experiment. The gaseous methanol and hydrogen chloride are fed to an insulated double pipe heat exchanger and heated to reaction temperature with a suitable heat transfer medium, such as a blend of about 40 percent diphenyl oxide and about 60 percent biphenylyl phenyl ether. Thermocouples are attached at intervals along the reactor tube length to measure the temperature at various depths in the catalyst bed. After mixing and heating in the double pipe heat exchanger the gaseous mixture is introduced into the top of the hydrochlorination reactor and passes through the catalyst, exiting as product methyl chloride, byproducts, unreacted feed gases and water vapor. The effluent gaseous mixture can be condensed by a suitable heat exchanger and separated to recover pure product and recycle feed gases.

EXAMPLE 1

The general reaction scheme described above was used. The initial 4 feet (1.22 meters) of the reactor was loaded with 60 m$^2$/g alumina and the remaining section of the reactor was filled with 200 m$^2$/g alumina. The flow rate for methanol was 3.94 lb/hr (1.79 kg/hr) and for hydrogen chloride was 5.3 lb/hr (2.41 kg/hr) at 50 psig. A reaction using a single catalyst zone with 200 m$^2$/g alumina was also run. The temperature profiles for these systems at 240° C. heat transfer fluid temperatures are shown in Table I. Additionally, the table shows the methanol conversion and the amount of dimethyl ether (DME) produced relative to methyl chloride (Ml). With this stratified catalyst system there is only a small broad hot spot instead of the typical large, narrow hot spot observed when the reactor is loaded with only alumina with surface area greater than 200 m$^2$/g.

TABLE I

| REACTOR DEPTH, ft. | BULK GAS TEMPERATURE, °C. | |
|---|---|---|
| | 200 m$^2$/g ALUMINA | 60 + 200 m$^2$/g ALUMINA |
| 1 | 370 | 256 |
| 2 | 272 | 265 |
| 4 | 241 | 252 |
| 6 | 239 | 246 |
| 9 | 239 | 242 |
| 12 | 239 | 241 |
| Methanol conv | 99.7% | 99.4% |
| DME/Ml ratio | 1591 ppm | 4967 ppm |

In a preferred embodiment wherein methanol and hydrogen chloride react to form methyl chloride, the process of the present invention utilizing an amorphous alumina catalyst system results in a long-lived catalyst. This catalyst is stable and the decreased temperature of the pressure drop. Further, the increase in average pore size decreases the conversion of amorphous alumina to boehmite.

EXAMPLE 2

The reactor described above is loaded as follows:
Fourteen weight percent KCl supported on silica is loaded into the first foot (0.3 m) of the reactor
Next 4.5 (1.4 m) feet is loaded with ZnCl$_2$/KCl supported on silica with 5 weight percent ZnCl$_2$ and a 1.1:1 molar ratio of KCl to ZnCl$_2$
Next 10 (3.04 m) feet is loaded with ZnCl$_2$/KCl supported on silica with 17.5 weight percent ZnCl$_2$ and a 1.0:1 molar ratio of KCl to ZnCl$_2$
The catalyst is dried overnight at 220° C. in nitrogen and conditioned for 15 minutes with HCl at 220° C.

In the gas phase using the above reactor scheme and general procedure, the proportions of methanol to hydrogen chloride and the reaction temperature are varied as shown in Table II below. The reactor effluent is analyzed by gas chromatography to determine the conversion obtained and the amount of dimethyl ether produced relative to the amount of methyl chloride produced. The results obtained are shown in Table II below. In Runs 1 and 2, a temperature profile is determined by measuring the temperature at various reactor depths as shown in Table III below.

TABLE II

| Run | Methanol (lb/hr) | HCl (lb/hr) | Exc HCl (%) | Temp (°C.) | Meth. Conv (%) | HCl Conversion [1] (%) | DME/MC [2] (ppm) |
|---|---|---|---|---|---|---|---|
| 1 | 8.00 | 10.00 | 10 | 220 | 94.2 | 87.1 | 7076 |
| 2 | 8.00 | 10.00 | 10 | 235 | 95.4 | 88.8 | 5930 |
| 3 | 3.92 | 5.57 | 25 | 220 | 99.1 | 83.9 | 2761 |
| 4 | 3.92 | 5.57 | 25 | 220 | 99.2 | — | 2097 |
| 5 | 3.92 | 4.91 | 10 | 220 | 98.0 | 89.1 | 4349 |
| 6 | 7.46 | 10.57 | 25 | 220 | 97.5 | 78.7 | 3598 |
| 7 | 5.83 | 7.78 | 17 | 220 | 97.6 | 84.0 | 4083 |
| 8 | 4.14 | 4.95 | 5 | 220 | 97.2 | 90.5 | 5620 |
| 9 | 4.24 | 4.84 | 0.3 | 220 | 96.9 | 92.1 | 5944 |
| 10 | 3.29 | 4.12 | 10 | 220 | 98.6 | 87.5 | 3494 |
| 11 | 3.29 | 3.67 | −2 | 220 | 96.8 | 93.9 | 6869 |
| 12 | 10.51 | 14.95 | 25 | 220 | 96.0 | 78.1 | 4341 |
| 13 | 10.51 | 11.72 | −2 | 220 | 89.9 | 88.8 | 8363 |

TABLE III

| REACTOR DEPTH, ft. | BULK GAS TEMPERATURE, °C. | |
|---|---|---|
| | 220° C. | 235° C. |
| 1 | 243 | 252 |

TABLE III-continued

| REACTOR DEPTH, ft. | BULK GAS TEMPERATURE, °C | |
|---|---|---|
| | 220° C. | 235° C |
| 2 | 242 | 254 |
| 4 | 238 | 250 |
| 6 | 259 | 269 |
| 9 | 228 | 238 |

The data in Table II above shows the effectiveness of the present invention utilizing a supported zinc chloride/potassium chloride catalyst in obtaining high methanol conversion and good selectivity. The ratio of dimethyl ether (DME) to methyl chloride is given in the last column and shows the parts of DME produced per million parts of methyl chloride. The data in Table III above shows that the reaction has been delocalized resulting in a moderation of any hot spots. This is accomplished without significant detrimental impact on methanol conversion or dimethyl ether by-product production.

EXAMPLE 3

A production scale reactor constructed of Iconel 600 consisting of 1,532 tubes, each having a diameter of 1.25 feet (0.38 m) and a length of 16 feet (4.9 m) is loaded with commercial grade 150 m²/g alumina and operated for a period of 126 days. To test the effect of alumina surface area on carbon formation, three individual tubes of the reactor are loaded with aluminas of surface areas of 125, 105 and 50 m²/g respectively, as shown in Table IV below. An analysis of the carbon content of the three test tubes along the depth of the reactor at the end of the 126 days run is given in Table IV below.

TABLE IV

| REACTOR DEPTH, ft. | CARBON CONTENT, (WT PERCENT) | | |
|---|---|---|---|
| | 125 m²/g Alumina | 125 m²/g Alumina | 125 m²/g Alumina |
| 3 | 19.41 | 13.78 | 8.44 |
| 4 | 12.76 | 6.37 | 3.91 |
| 5 | 8.47 | 1.35 | 0.78 |
| 6 | 3.90 | 0.44 | 0.16 |

The data shown above demonstrates that lower surface area aluminas moderate the amount of decomposition which occurs, leading to product decomposition.

What is claimed is:

1. A process for preparing methyl halide from methanol and a hydrogen halide which process comprises contacting said methanol and said hydrogen halide with a hydrohalogenation catalyst.system having at least two zones wherein the catalytic activity of each zone is lower than that of each succeeding zone, under reaction conditions sufficient to form the methyl halide.

2. The process of claim 1 wherein the catalyst has at least three zones.

3. The process of claim 1 wherein the catalyst has from two to four zones.

4. The process of claim 1 wherein the catalyst is selected from the group consisting of amorphous alumina and supported potassium chloride/zinc chloride.

5. The process of claim 4 wherein the catalyst system comprises amorphous alumina; has three zones and the surface area of the alumina in the first zone is from 40 to 100 m²/g ; the surface area of the alumina in the second zone is from 70 to 150 m²/g ; and the surface are of the alumina in the third zone is from 150 to 250 m²/g, with the proviso that the surface area of the alumina in each zone is greater than that of the alumina in the processing zone.

6. The process of claim 5 wherein from 10 to 30 percent of the catalyst is in each of the first and second zones and 40 to 80 percent of the catalyst is in the third zone.

7. The process of claim 4 wherein the catalyst is amorphous alumina and has a minimum pore size distribution in the area of 100 angstroms (Å) or less.

8. The process of claim 4 wherein the catalyst is supported zinc chloride/potassium chloride.

* * * * *

UNITED STATES PATENT AND TRADEMARK OFFICE
CERTIFICATE OF CORRECTION

PATENT NO. : 5,109,138
DATED : April 28, 1992
INVENTOR(S) : Michael T. Holbrook et al.

It is certified that error appears in the above-identified patent and that said Letters Patent is hereby corrected as shown below:

Column 10, line 34, "zone is greater than that of the alumina in the processing", should correctly read --zone is greater than that of the alumina in the preceding--.

Signed and Sealed this

Twenty-fourth Day of August, 1993

Attest:

BRUCE LEHMAN

Attesting Officer

Commissioner of Patents and Trademarks